United States Patent [19]

Van den Eynde et al.

[11] Patent Number: 5,610,013
[45] Date of Patent: Mar. 11, 1997

[54] METHOD FOR DIAGNOSING A DISORDER BY DETERMINING EXPRESSION OF GAGE TUMOR REJECTION ANTIGEN PRECURSORS

[75] Inventors: Benoit Van den Eynde; Thierry Boon-Falleur, both of Brussels, Belgium

[73] Assignee: Ludwig Institute for Cancer Research, New York, N.Y.

[21] Appl. No.: 250,162

[22] Filed: May 27, 1994

Related U.S. Application Data

[63] Continuation-in-part of Ser. No. 96,039, Jul. 22, 1993, abandoned.

[51] Int. Cl.$^6$ .............................. C12Q 1/68; C12N 5/00; C12N 1/20; C07H 19/00
[52] U.S. Cl. ........................ 435/6; 435/7.1; 435/252.3; 435/252.33; 435/320.1; 435/325; 435/365; 435/358; 435/362; 536/23.5
[58] Field of Search ...................... 435/6, 320.1, 240.2, 435/252.3, 252.33, 7.1; 536/23.5

[56] References Cited

PUBLICATIONS

Herin et al., "Production of Stable Cytolytic T–Cell Clones–Directed Against Autologous Human Melanoma", Int. J. Cancer 39: 390–396 (1987).

Wolfel et al., "Lysis of Human Melanoma Cells By Autologous–Cytolytic T Cell Clones", J. Exp. Med. 170: 797–810 (Sep. 1989).

Van Den Eynde et al., "Presence On a Human Melanoma of Multiple–Antigens Recognized by Autologous CTL", Int. J. Cancer 44: 634–640 (1989).

Van der Bruggen, et al., "A Gene Encoding An Antigen Recognized–By Cytolytic T Lymphocytes on a Human Melanoma", Science 254: 1643–1647 (Dec. 1991).

Brasseur et al., "Human Gene MAGE–1, which codes for a tumor–rejection antigen, is expressed by some breast tumors", Int. J. Cancer 52: 839–841 (1992).

Traversari et al., "Transfection and expression of a gene–coding for a human melanoma antigen recognized by autologous cytolytic T lymphocytes", Immunogenetics 35: 145–152 (1992).

Traversari et al., "A Nonapeptide Encoded by Human Gene MAGE–1–Is Recognized on HLA–A1 By Cytolytic T Lymphocytes Directed Against Tumor Antigen MZ2–E", J. Exp. Med. 176: 1453–1457 (Nov. 1992).

*Primary Examiner*—Keith D. Hendricks
*Assistant Examiner*—Hyosuk Kim
*Attorney, Agent, or Firm*—Felfe & Lynch

[57] ABSTRACT

A new family of tumor rejection antigen precursors, and the nucleic acid molecules which code for them, are disclosed. These tumor rejection antigen precursors are referred to as GAGE tumor rejection antigen precursors, and the nucleic acid molecules which code for them are referred to as GAGE coding molecules. Various diagnostic and therapeutic uses of the coding sequences and the tumor rejection antigens, and their precursor molecules are described.

37 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 648 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO: 1:

```
AGCTGCCGTC   CGGACTCTTT   TTCCTCTACT   GAGATTCATC   TGTGTGAAAT   ATGAGTTGGC        60

GAGGAAGATC   GACCTATCGG   CCTAGACCAA   GACGCTACGT   AGAGCCTCCT   GAAATGATTG       120

GGCCTATGCG   GCCCGAGCAG   TTCAGTGATG   AAGTGGAACC   AGCAACACCT   GAAGAAGGGG       180

AACCAGCAAC   TCAACGTCAG   GATCCTGCAG   CTGCTCAGGA   GGGAGAGGAT   GAGGGAGCAT       240

CTGCAGGTCA   AGGGCCGAAG   CCTGAAGCTG   ATAGCCAGGA   ACAGGGTCAC   CCACAGACTG       300
```

| | | | | | | |
|---|---|---|---|---|---|---|
| GGTGTGAGTG | TGAAGATGGT | CCTGATGGGC | AGGAGATGGA | CCCGCCAAAT | CCAGAGGAGG | 360 |
| TGAAAACGCC | TGAAGAAGAG | ATGAGGTCTC | ACTATGTTGC | CCAGACTGGG | ATTCTCTGGC | 420 |
| TTTTAATGAA | CAATTGCTTC | TTAAATCTTT | CCCCACGGAA | ACCTTGAGTG | ACTGAAATAT | 480 |
| CAAATGGCGA | GAGACCGTTT | AGTTCCTATC | ATCTGTGGCA | TGTGAAGGGC | AATCACAGTG | 540 |
| TTAAAAGAAG | ACATGCTGAA | ATGTTGCAGG | CTGCTCCTAT | GTTGGAAAAT | TCTTCATTGA | 600 |
| AGTTCTCCCA | ATAAAGCTTT | ACAGCCTTCT | GCAAAGAAAA | AAAAAAA | | 648 |

( 2 ) INFORMATION FOR SEQ ID NO: 2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO: 2:

AGACGCTACG TAGAGCCT     18

( 2 ) INFORMATION FOR SEQ ID NO: 3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO: 3:

CCATCAGGAC CATCTTCA     18

METHOD FOR DIAGNOSING A DISORDER BY DETERMINING EXPRESSION OF GAGE TUMOR REJECTION ANTIGEN PRECURSORS

RELATED APPLICATION

This application is a continuation-in-part of patent application Se. No. 08/096,039 filed Jul. 22, 1993 now abandoned.

FIELD OF THE INVENTION

This invention relates to a nucleic acid molecule which codes for a tumor rejection antigen precursor. More particularly, the invention concerns genes, whose tumor rejection antigen precursor is processed, inter alia, into at least one tumor rejection antigen that is presented by HLA-Cw6 molecules. The genes in question do not appear to be related to other known tumor rejection antigen precursor coding sequences.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257:880 (1992); Fremont et al., Science 257:919 (1992); Matsumura et al., Science 257:927 (1992); Latron et al., Science 257:964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35:145 (1992); van der Bruggen et al., Science 254:1643 (1991), for further information on this family of genes. Also, see U.S. patent application Ser. No. 807,043, filed Dec. 12, 1991, now U.S. Pat. No. 5,342,774.

In U.S. patent application Ser. No. 938,334, the disclosure of which is incorporated by reference, it is explained that the MAGE-1 gene codes for a tumor rejection antigen precursor which is processed to nonapeptides which are presented by the HLA-A1 molecule. The reference teaches that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed. This second TRA is presented by HLA-C clone 10 molecules. The disclosure shows that a given TRAP can yield a plurality of TRAs.

U.S. patent application Ser. No. 994,928, filed Dec. 22, 1992, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993, and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 08/079,110, filed Jun. 17, 1993 and incorporated by reference herein, an unrelated tumor rejection antigen precursor, the so-called "BAGE" precursor is described. The BAGE precursor is not related to the MAGE family.

The work which is presented by the papers, patent, and patent applications cited supra deals, in large part, with the MAGE family of genes, and the unrelated BAGE gene. It has now been found, however, that additional tumor rejection antigen precursors are expressed by cells. These tumor rejection antigen precursors are referred to as "GAGE" tumor rejection antigen precursors. They do not show homology to either the MAGE family of genes or the BAGE gene. Thus the present invention relates to genes encoding such TRAPs, the tumor rejection antigen precursors themselves as well as applications of both.

The invention is elaborated upon further in the disclosure which follows.

DETAILED DESCRIPTION OF PREFERRED EMBODIMENTS

Example 1

A melanoma cell line, MZ2-MEL was established from melanoma cells taken from patient MZ2, using standard methodologies. This cell line is described, e.g., in PCT Application PCT/US92/04354, filed May 22, 1992, published Nov. 26, 1992, and incorporated by reference in its entirety. Once the cell line was established, a sample thereof was irradiated, so as to render it non-proliferative. These irradiated cells were then used to isolate cytolytic T cell clones ("CTLs") specific thereto.

A sample of peripheral blood mononuclear cells ("PBMCs") was taken from patient MZ2, and contacted to the irradiated melanoma cells. The mixture was observed for lysis of the melanoma cells, which indicated that CTLs specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 μCi/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 8% CO$_2$ atmosphere.

Plates were centrifuged again, and 100 ul aliquots of supernatant were collected and counted. Percentage of $^{51}$Cr release was calculated as follows:

$$\% \ ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology. The CTL clone MZ2-CTL 76/6 was thus isolated. The clone is referred to as "76/6" hereafter.

The same method was used to test target K562 cells, as well as the melanoma cell line. FIG. 1 shows that this CTL clone recognizes and lyses the melanoma cell line, i.e. MZ2-MEL but not K562. The clone was then tested against other melanoma cell lines and autologous EBV-transformed B cells in the same manner described supra. FIG. 1 shows that autologous B cells, transformed by Epstein Barr Virus ("EBV") were not lysed, and that while MZ2-MEL 3.0 was lysed by CTL clone 76/6, the cell line MZ2-MEL.4F$^-$, a variant which does not express antigen F was not. Hence, the clone appears to be specific for this antigen.

The results presented supra are inconclusive as to which HLA molecule presents the TRA. The lysed cell line, i.e., MZ2-MEL, is known to express HLA-A1, HLA-A29, HLA-B37, HLA-B44, HLA-Cw6, and HLA-C clone 10. In experiments not reported here but which follow the protocol of this example, a subline of MZ2-MEL was tested, which had lost expression of HLA molecules A29, B44, and C clone 10. The subline was lysed, thus indicating that the presenting molecule should be one of A1, B37, or Cw6.

Example 2

Further studies were carried out to determine if 76/6 also produced tumor necrosis factor ("TNF") when contacted with target cells. The method used was that described by Traversari et al., Immunogenetics 35:145–152 (1992), the disclosure of which is incorporated by reference. Briefly, samples of the CTL line were combined with samples of a target cell of interest in culture medium. After 24 hours, supernatant from the cultures was removed, and then tested on TNF-sensitive WEHI cells. Cell line MZ2.-MEL.43, a subclone of the MZ2-MEL cell line discussed supra as well as in the cited references, gave an extremely strong response, and was used in the following experiments.

Example 3

The results from Example 2 indicated that MZ2.MEL.43 presented the target antigen of interest. As such, it was used as a source of total mRNA to prepare a cDNA library.

Total RNA was isolated from the cell line. The mRNA was isolated using an oligo-dT binding kit, following well recognized techniques. Once the mRNA was secured, it was transcribed into cDNA, via reverse transcription, using an oligo dT primer containing a NotI site, followed by second strand synthesis. The cDNA was then ligated to a BstXI adaptor, digested with NotI, size fractionated on a Sephacryl S-500 HR column, and then cloned, undirectionally, into the BstXI and Not I sites of pcDNA-I-Amp. The recombinant plasmid was then electroporated into DH5α E. coli bacteria. A total of 1500 pools of 100 recombinant bacteria were seeded in microwells. Each contained about 100 cDNAs, because nearly all bacteria contained an insert.

Each pool was amplified to saturation and plasmid DNA was extracted by alkaline lysis and potassium acetate precipitation, without phenol extraction.

Example 4

Following preparation of the library described in Example 3, the cDNA was transfected into eukaryotic cells. The transfections, described herein, were carried out in duplicate. Samples of COS-7 cells were seeded, at 15,000 cells/ well into tissue culture flat bottom microwells, in Dulbecco's modified Eagles Medium ("DMEM") supplemented with 10% fetal calf serum. The cells were incubated overnight at 37° C., medium was removed and then replaced by 50 μl/well of DMEM medium containing 10% Nu serum, 400 μg/ml DEAE-dextran, and 100 μM chloroquine, plus 100 ng of the plasmids. As was indicated supra, the lysis studies did not establish which HLA molecule presented the antigen. As a result, cDNA for each of the HLA molecules which could present the antigen (A1, B37, Cw6) was used, separately, to cotransfect the cells. Specifically, one of 28 ng of cDNA for HLA-A1, cloned into pCD-SRα was used, as were 50 ng of cDNA for HLA-B37 in pcDNA-I-Amp, or 75 ng of cDNA for HLA-Cw6 in pcDNA-I-Amp, using the same protocol as was used for transfection with the library.

Transfection was made in duplicate wells, but only 500 pools of the HLA-Cw6 transfectants could be tested in single wells. Following four hours of incubation at 37° C., the medium was removed, and replaced by 50 μl of PBS containing 10% DMSO. This medium was removed after two minutes and replaced by 200 μl of DMEM supplemented with 10% FCS.

Following this change in medium, COS cells were incubated for 24–48 hours at 37° C. Medium was then discarded, and 1000–3000 cells of CTL clone 76/6 were added, in 100 μl of Iscove's medium containing 10% pooled human serum supplemented with 20–30 U/ml of IL-2. Supernatant was removed after 24 hours, and TNF content was determined in an assay on WEHI cells, as described by Traversari et al., Immunogenetics 35:145–152 (1992), the disclosure of which is incorporated by reference.

The 1500 pools transfected with HLA-A1, and the 1500 pools transfected with HLA-B37, stimulated TNF release to a concentration of 15–20 pg/ml, or 2–6 pg/ml, respectively. Most of the HLA-Cw6 transfectants yielded 3–20 pg/ml, except for one pool, which yielded more than 60 pg/ml. This pool was selected for further work.

Example 5

Figure 1A:
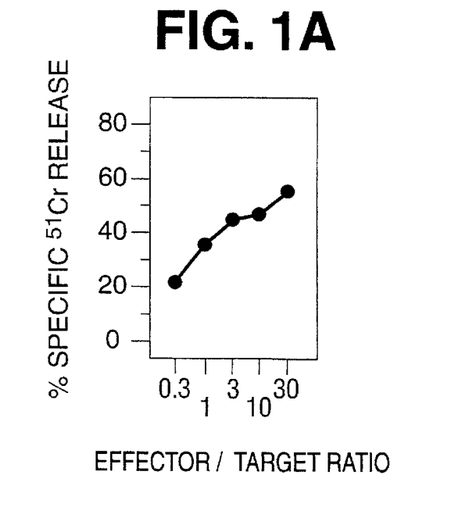
FIG. 1 sets forth lysis studies using CTL clone 76/6.
Figure 1B:
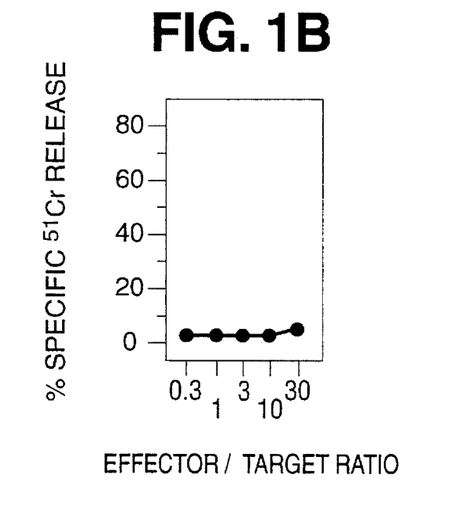
Figure 1C:
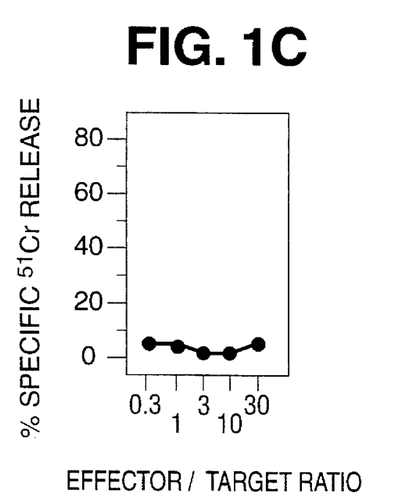
Figure 1D:
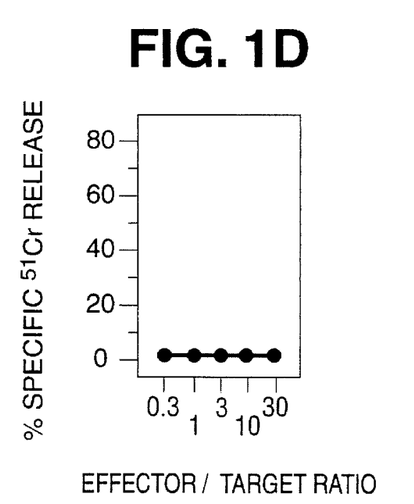
Figure 2:
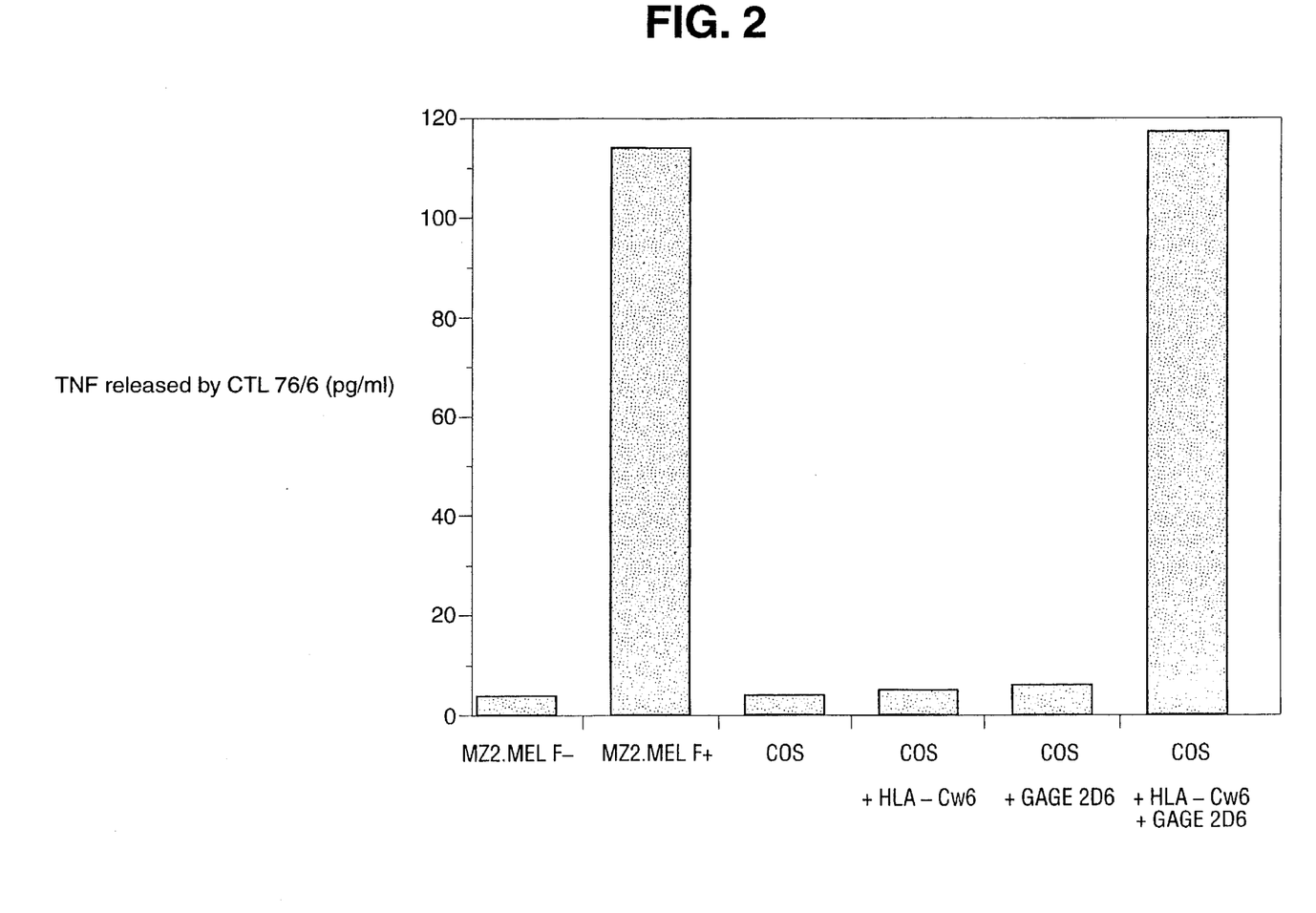
FIG. 2 shows tumor necrosis factor ("TNF") release assays obtained with various transfectants and controls.

The bacteria of the selected pool were cloned, and 600 clones were tested. Plasmid DNA was extracted therefrom, transfected into a new sample of COS cells in the same manner as described supra, and the cells were again tested for stimulation of CTL clone 76/6. Ninety-four positive clones were found. One of these, referred to as cDNA clone 2D6, was tested further. In a comparative test COS cells were transfected with cDNA clone 2D6 and the HLA-Cw6, HLA-Cw6 alone, or 2D6, alone. Control cell lines MZ2-MEL F$^-$ and MZ2-MEL F$^+$ were also used. TNF release into CTL supernatant was measured by testing it on WEHI cells, as referred to supra. The optical density of the surviving WEHI cells was measured using MTT. FIG. 2 shows that the COS cells transfected with HLA-Cw6 and cDNA-2D6, and the cell line MZ2-MEL F$^+$ stimulated TNF release from CTL clone 76/6, indicating that HLA-Cw6 presented the subject TRA.

Example 6

The cDNA 2D6 was sequenced following art known techniques. A sequence search revealed that the plasmid insert showed no homology to known genes or proteins. SEQUENCE ID NO: 1 presents cDNA nucleotide information for the identified gene, referred to hereafter as "GAGE". A putative open reading frame is located at bases 51–467 of the molecule.

Example 7

Following sequencing of the cDNA, as per Example 6, experiments were carried out to determine if cells of normal tissues expressed the gene. To determine this, Northern blotting was carried out on tissues and tumor cell lines, as indicated below. The blotting experiments used cDNA for the complete sequence of SEQ ID NO: 1. PCR was then used to confirm the results.

TABLE 1

| Expression of gene GAGE | |
|---|---|
| Normal tissues | |
| PHA-activated T cells | – |
| CTL clone 82/30 | – |
| Liver | – |
| Muscle | – |
| Lung | – |
| Brain | – |
| Kidney | – |
| Placenta | – |
| Heart | – |
| Skin | – |
| Testis | + |
| Tumor cell lines | |
| Melanoma | 7/16 |
| Lung Carcinoma | 1/6 |

TABLE 1-continued

| Expression of gene GAGE | |
|---|---|
| Sarcoma | 0/1 |
| Thyroid medullary carcinoma | 0/1 |
| Tumor samples | |
| Melanoma | 1/1 |

Example 8

Detailed analysis of normal tissues and tumors was carried out by applying polymerase chain reaction ("PCR") and the GAGE gene information described supra.

First, total RNA was taken from the particular sample, using art recognized techniques. This was used to prepare cDNA. The protocol used to make the cDNA involved combining 4 ul of reverse transcriptase buffer 5x, 1 ul of each dNTP, (10 mM), 2 ul of dithiothreitol (100 mM), 2 ul of dT-15 primer (20 um), 0.5 ul of RNasin (40 units/ul), and 1 ul of M-MLV reverse transcriptase (200 units/ul). Next, 6.5 ul of template RNA (1 ug/3.25 ul water, or 2 ug total template RNA) was added. The total volume of the mixture was 20 ul. This was mixed and incubated at 42° C. for 60 minutes, after which it was chilled on ice. A total of 80 ul of water was then added, to 100 ul total. This mixture was stored at −20° C. until used in PCR.

To carry out PCR, the primers 5'-AGA CGC TAC GTA GAG CCT-3' (sense) and 5'-CCA TCA GGA CCA TCT TCA-3" (antisense) SEQ ID NOS: 2 and 3, respectively, were used. The reagents included 30.5 ul water, 5 ul of PCR buffer 10x, 1 ul of each dNTP (10 uM), 2.5 ul of each primer (20 uM), and 0.5 ul of polymerizing enzyme "Dynazyme" (2 units/ul). The total volume was 45 ul. A total of 5 ul of cDNA was added (this corresponded to 100 ng total RNA). The mixture was combined, and layered with one drop of mineral oil. The mixture was transferred to a thermocycler block, preheated to 94° C., and amplification was carried out for 30 cycles, each cycle consisting of the following:

first denaturation: 94° C., 4 min.

denaturation: 94° C., 1 min.

annealing: 55° C., 2 min.

extension: 72° C., 3 min.

final extension: 72° C., 15 min.

Following the cycling, 10 ul aliquots were run on a 1.5% agarose gel, stained with ethidium bromide.

cDNA amplified using the primers set forth supra yields a 238 base pair fragment. There is no amplification of contaminating genomic DNA, if present.

The results are presented in Table 2, which follows. They confirm that the only normal tissue which expresses GAGE is testis, whereas a number of tumors, including melanoma, lung, breast, larynx, pharynx, sarcoma, testicular seminoma, bladder and colon express the gene. Thus, any one of these tumors can be assayed for by assaying for expression of the GAGE gene.

TABLE 2

| RT-PCR analysis of the expression of gene GAGE | |
|---|---|
| NORMAL TISSUES | |
| Heart | – |
| Brain | – |

TABLE 2-continued

RT-PCR analysis of the expression of gene GAGE

| Liver | – |
| --- | --- |
| Lung | – |
| Kidney | – |
| Spleen | – |
| Lymphocytes | – |
| Bone marrow | – |
| Skin | – |
| Naevus | – |
| Melanocytes | – |
| Fibroblasts | – |
| Prostate | – |
| Testis | + |
| Ovary | – |
| Breast | – |
| Adrenals | – |
| Muscle | – |
| Placenta | – |
| Umbilical Cord | – |

| TUMORS | Cell lines | Tumor samples | |
| --- | --- | --- | --- |
| Melanoma | 40/63 | 46/146 | (32%) |
| Lung cancer | | | |
| Epidermoid carcinoma | | 10/41 | (24%) |
| Adenocarcinoma | | 4/18 | |
| Small Cell Lung Cancer | 6/23 | 0/2 | |
| Breast cancer | | 15/146 | (10%) |
| Head and Neck tumor | | | |
| Larynx | | 6/15 | (40%) |
| Pharynx | | 3/13 | |
| Sarcoma | 1/4 | 6/18 | (33%) |
| Testicular seminoma | | 6/6 | (100%) |
| Bladder cancer | | 5/37 | (14%) |
| Prostate cancer | | 2/20 | |
| Colon carcinoma | 5/13 | 0/38 | |
| Renal cancer | 0/6 | 0/45 | |
| Leukemia | 3/6 | 0/19 | |

The foregoing examples show the isolation of a nucleic acid molecule which codes for a tumor rejection antigen precursor. This "TRAP" coding molecule, however, is not homologous with any of the previously disclosed MAGE and BAGE coding sequences described in the references set forth supra. Hence, one aspect of the invention is an isolated nucleic acid molecule which comprises the nucleotide sequence set forth in SEQ ID NO: 1. This sequence is neither a MAGE nor a BAGE coding sequence, as will be seen by comparing it to the sequence of any of these genes as described in the cited references. Also a part of the invention are those nucleic acid sequences which also code for a non-MAGE and non-BAGE tumor rejection antigen precursor but which hybridize to a nucleic acid molecule containing the described nucleotide sequence, under stringent conditions. The term "stringent conditions" as used herein refers to parameters with which the art is familiar. More specifically, stringent conditions, as used herein, refers to hybridization in 1M NaCl, 1% SDS, and 10% dextran sulfate. This is followed by two washes of the filter at room temperature for 5 minutes, in 2xSSC, and one wash for 30 minutes in 2xSSC, 0.1% SDS. There are other conditions, reagents, and so forth which can be used, which result in the same or higher degree of stringency. The skilled artisan will be familiar with such conditions, and, thus, they are not given here.

It will also be seen from the examples that the invention embraces the use of the sequences in expression vectors, as well as to transfect host cells and cell lines, be these prokaryotic (e.g., *E. coli*), or eukaryotic (e.g., CHO or COS cells). The expression vectors require that the pertinent sequence, i.e., those described Supra, be operably linked to a promoter. As it has been found that human leukocyte antigen HLA-Cw6 presents a tumor rejection antigen derived from these genes, the expression vector may also include a nucleic acid sequence coding for HLA-Cw6. In a situation where the vector contains both coding sequences, it can be used to transfect a cell which does not normally express either one. The tumor rejection antigen precursor coding sequence may be used alone, when, e.g., the host cell already expresses HLA-Cw6. Of course, there is no limit on the particular host cell which can be used. As the vectors which contain the two coding sequences may be used in HLA-Cw6 presenting cells if desired, and the gene for tumor rejection antigen precursor can be used in host cells which do not express HLA-Cw6.

The invention also embraces so called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the TRAPs of the invention from the previously described MAGE and BAGE materials, the invention shall be referred to as the GAGE family of genes and TRAPs. Hence, whenever "GAGE" is used herein, it refers to the tumor rejection antigen precursors coded for by the previously described sequences. "GAGE coding molecule" and similar terms, are used to describe the nucleic acid molecules themselves.

The invention as described herein has a number of uses, some of which are described herein. First, the invention permits the artisan to diagnose a disorder characterized by expression of the TRAP. These methods involve determining expression of the TRAP gene, and/or TRAs derived therefrom, such as a TRA presented by HLA-Cw6. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred. An alternate method for determination is a TNF release assay, of the type described supra. To carry out the assay, it is preferred to make sure that testis cells are not present, as these normally express GAGE. This is not essential, however, as one can routinely differentiate between testis and other cell types. Also, it is practically impossible to have testis cells present in non-testicular sample.

The isolation of the TRAP gene also makes it possible to isolate the TRAP molecule itself, especially TRAP molecules containing the amino acid sequence coded for by SEQ ID NO: 1. These isolated molecules when presented as the TRA, or as complexes of TRA and HLA, such as HLA-Cw6, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provide a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular. Melanoma is well known as a cancer of pigment producing cells.

Therapeutic approaches based upon the disclosure are premised on a response by a subject's immune system, leading to lysis of TRA presenting cells, such as HLA-Cw6 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5):1917 (1986); Riddel et al., Science 257:238 (Jul. 10, 1992); Lynch et al., Eur. J. Immunol. 21:1403–1410 (1991); Kast et al., Cell 59:603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex, where the complex contains the pertinent HLA molecule. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a GAGE sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a GAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88:110–114 (January, 1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-Cw6 presenting cells which then present the HLA/peptide complex of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for screening for a disorder characterized by expression of a GAGE tumor rejection antigen precursor, comprising contacting a sample which does not contain normal testes cells from a subject believed to have said disorder, with a probe which hybridizes to a cDNA or mRNA molecule which codes for said GAGE tumor rejection antigen precursor, and determining hybridization of said probe to said cDNA or mRNA, wherein said hybridization is an indication of said disorder in said subject.

2. Method for screening for a disorder characterized by expression of a tumor rejection antigen precursor coded for by a cDNA molecule comprising nucleotides 51–476 of SEQ ID NO: 1, comprising contacting a sample from a subject believed to suffer from said disorder with an antibody specific for an expression product of SEQ ID NO: 1, and determining binding between said antibody and said expression product as an indication of possible presence of said disorder in said subject.

3. The method of claim 1, wherein said disorder is melanoma.

4. The method of claim 2, wherein said disorder is melanoma.

5. The method of claim 1, wherein said disorder is breast cancer.

6. The method of claim 2, wherein said disorder is breast cancer.

7. The method of claim 1, wherein said disorder is a larynx or pharynx tumor.

8. The method of claim 2, wherein said disorder is a larynx or pharynx tumor.

9. The method of claim 1, wherein said disorder is sarcoma.

10. The method of claim 2, wherein said disorder is sarcoma.

11. The method of claim 1, wherein said disorder is bladder cancer.

12. The method of claim 2, wherein said disorder is bladder cancer.

13. The method of claim 1, wherein said disorder is colon carcinoma.

14. The method of claim 2, wherein said disorder is colon carcinoma.

15. Isolated nucleic acid molecule selected from the group consisting of SEQ ID NO: 2 and SEQ ID NO: 3.

16. An isolated nucleic acid molecule consisting of the nucleotide sequence set forth in SEQ ID NO: 1.

17. An isolated nucleic acid molecule, the complementary sequence which hybridizes, under stringent conditions, to the nucleic acid molecule set forth in SEQ ID NO: 1, and codes for a tumor rejection antigen precursor, with the proviso that said isolated nucleic acid molecule does not code for a MAGE tumor rejection antigen precursor or a BAGE tumor rejection antigen precursor.

18. An isolated nucleic acid molecule consisting of nucleotides 51–467 of SEQ ID NO: 1.

19. An isolated mRNA molecule which is complementary to the isolated nucleic acid molecule of claim 16.

20. A host cell transfected with the isolated nucleic acid molecule of claim 16.

21. A host cell transfected with the isolated nucleic acid molecule of claim 17.

22. A host cell transfected with the isolated nucleic acid molecule of claim 18.

23. An expression vector comprising the isolated nucleic acid molecule of claim 16 operably linked to a promoter.

24. An expression vector comprising the isolated nucleic acid molecule of claim 17 operably linked to a promoter.

25. An expression vector comprising the isolated nucleic acid molecule of claim 18 operably linked to a promoter.

26. The host cell of claim 20, wherein said host cell is a mammalian cell which expresses HLA-Cw6.

27. The host cell of claim 21, wherein said host cell is a mammalian cell which expresses HLA-Cw6.

28. The host cell of claim 22, wherein said host cell is a mammalian cell which expresses HLA-Cw6.

29. The expression vector of claim 23, further comprising a nucleic acid molecule which codes for HLA-Cw6.

30. The expression vector of claim 24, further comprising a nucleic acid molecule which codes for HLA-Cw6.

31. The expression vector of claim 25, further comprising a nucleic acid molecule which codes for HLA-Cw6.

32. Expression kit comprising a separate portion of each of
   (i) the expression vector of claim 23, and
   (ii) a nucleic acid molecule which encodes HLA-Cw6.

33. Expression kit comprising a separate portion of each of
   (i) the expression vector of claim 24, and,
   (ii) a nucleic acid molecule which encodes HLA-Cw6.

34. Expression kit comprising
   (i) the expression vector of claim 25, and
   (ii) a nucleic acid molecule, which encodes HLA-Cw6.

35. The method of claim 2, wherein said expression product is a GAGE tumor rejection antigen precursor.

36. The method of claim 35, wherein said agent is an antibody.

37. Method for screening for a disorder characterized by expression of a tumor rejection antigen encoded by a cDNA molecule comprising nucleotides 51–476 of SEQ ID NO: 1, comprising contacting a cDNA or mRNA molecule containing sample from a subject with a nucleic acid hybridization probe which hybridizes to a cDNA molecule comprising nucleotides 51–476 of SEQ ID NO: 1, and determining binding of said hybridization probe to said cDNA or mRNA molecules as an indication of possible presence of said disorder in said subject.

* * * * *

UNITED STATES PATENT AND TRADEMARK OFFICE
CERTIFICATE OF CORRECTION

PATENT NO : 5,610,013
DATED : March 11, 1997
INVENTOR(S) : Van Den Eynde et al.

It is certified that error appears in the above-identified patent and that said Letters Patent is hereby corrected as shown below:

Column 14, lines 11 and 12,          delete Claim 36 in its totality.

Signed and Sealed this

Eighth Day of June, 1999

*Attest:*

Q. TODD DICKINSON

*Attesting Officer*     *Acting Commissioner of Patents and Trademarks*